United States Patent
Patterson

(10) Patent No.: US 9,177,185 B2
(45) Date of Patent: Nov. 3, 2015

(54) PASSIVE WIRELESS SENSORS FOR CHEMICAL AND BIOLOGICAL AGENTS AND WIRELESS SYSTEMS INCLUDING THE PASSIVE WIRELESS SENSORS

(71) Applicant: University of Dayton, Dayton, OH (US)

(72) Inventor: Mark Alan Patterson, Beavercreek, OH (US)

(73) Assignee: University of Dayton, Dayton, OH (US)

( * ) Notice: Subject to any disclaimer, the term of this patent is extended or adjusted under 35 U.S.C. 154(b) by 124 days.

(21) Appl. No.: 13/949,907

(22) Filed: Jul. 24, 2013

(65) Prior Publication Data

US 2014/0062666 A1 Mar. 6, 2014

Related U.S. Application Data

(60) Provisional application No. 61/675,565, filed on Jul. 25, 2012.

(51) Int. Cl.
*H04Q 5/22* (2006.01)
*G08B 1/08* (2006.01)
(Continued)

(52) U.S. Cl.
CPC ........ *G06K 7/10366* (2013.01); *G01N 33/0031* (2013.01); *G06K 19/0716* (2013.01); *G01N 2291/0255* (2013.01); *G01N 2291/0256* (2013.01)

(58) Field of Classification Search
CPC . G01N 29/00; G01N 9/24; G01N 2015/0046; G01N 2015/0065; G01N 22/00; G01N 27/3275; G01N 27/3278; G01N 2223/419; G01N 23/046; G01N 2291/0255; G01N 29/022; G01N 33/0031; G01N 2291/106; G06K 19/0716; G06K 7/10366; G06K 19/0717; H01Q 9/28

USPC .............. 340/10.1, 572.1, 505, 10.3, 539.26, 340/545.2, 539.16, 10.41, 572.4; 422/82.02, 52, 73, 82.08, 82.11, 503, 422/83, 94, 98; 436/164, 177, 43, 63; 250/214.1, 251, 576; 73/23.2, 24.01
See application file for complete search history.

(56) References Cited

U.S. PATENT DOCUMENTS 6,359,444 B1 * 3/2002 Grimes .......................... 324/633
7,922,975 B2 * 4/2011 Subramanyam ........... 422/82.01
(Continued)

OTHER PUBLICATIONS

NAECON Report, "A Passive Wireless Sensor Platform for Chemical and Biological Agents", Patterson et al., University of Dayton, Dayton, OH 45469 dated Jul. 26, 2012.
(Continued)

*Primary Examiner* — Jennifer Mehmood
*Assistant Examiner* — Mirza Alam
(74) *Attorney, Agent, or Firm* — Dinsmore & Shohl LLP

(57) ABSTRACT

Wireless sensors for detection of an analyte may include a sensor receiving antenna configured to receive interrogation pulses having an interrogation frequency, a DC converter, a relaxation oscillator circuit electrically, and a sensor transmitting antenna. The relaxation oscillator circuit may include a capacitance element that defines a response-pulse frequency of the wireless sensor. The capacitance element may include an interdigitated capacitor coated with a detection layer of a functional material having a dielectric constant that defines the dielectric constant of the interdigitated capacitor. This dielectric constant changes when the functional material is exposed to the analyte, thereby changing the response-pulse frequency of the relaxation oscillator circuit to an analyte-exposure frequency indicative of the exposure of the functional material to the analyte. Wireless systems for detecting an analyte may include a wireless sensor that communicates with an interrogation module.

20 Claims, 11 Drawing Sheets

(51) Int. Cl.

| | | |
|---|---|---|
| | *G08B 13/08* | (2006.01) |
| | *G01N 7/00* | (2006.01) |
| | *G01N 21/00* | (2006.01) |
| | *G06K 7/10* | (2006.01) |
| | *G01N 33/00* | (2006.01) |
| | *G06K 19/07* | (2006.01) |

(56) References Cited

U.S. PATENT DOCUMENTS

2003/0040004 A1* 2/2003 Hefti et al. .................. 435/6
2005/0088299 A1* 4/2005 Bandy et al. ............. 340/539.16
2006/0186342 A1* 8/2006 Burger et al. ............. 250/370.01
2007/0090927 A1* 4/2007 Potyrailo et al. ........... 340/10.41
2007/0180892 A1* 8/2007 Sunshine ..................... 73/24.01
2009/0256679 A1* 10/2009 Potyrailo et al. ............. 340/10.1

OTHER PUBLICATIONS

Dissertation by Mark Alan Patterson, titled, "A Passive Wireless Platform for Chemical-Biological Sensors", dated Dec. 2012.

* cited by examiner

US 9,177,185 B2

PASSIVE WIRELESS SENSORS FOR CHEMICAL AND BIOLOGICAL AGENTS AND WIRELESS SYSTEMS INCLUDING THE PASSIVE WIRELESS SENSORS

CROSS-REFERENCES TO RELATED APPLICATIONS

This application claims the benefit of priority under 35 U.S.C. §119(e) to U.S. Provisional Application Ser. No. 61/675,565, filed Jul. 25, 2012.

STATEMENT REGARDING FEDERALLY SPONSORED RESEARCH OR DEVELOPMENT

This invention was made with government support under contract FA8650-10-2-7028, Project 8, awarded by The Air Force Research Laboratories (AFRL). The government has certain rights in the invention.

TECHNICAL FIELD

This specification relates generally to chemical and biological sensors and, more particularly, to passive wireless sensors for chemical and biological agents and to sensor systems including the passive wireless sensors.

BACKGROUND

Chemical-biological sensors represent a rapidly expanding field with an estimated 60% annual growth rate in fields such as the health care industry, homeland security, the food industry, the military, and environmental monitoring. Sensors in the health care industry are currently a $1 billion/year market, for example. There is an increasing demand for inexpensive and reliable sensors for doctor's offices, emergency rooms, and operating rooms. Homeland security has been a recent thrust in sensor development. It is desirable to install real time monitoring and alarm systems at potential terrorist sites to detect specific analytes such as ricin, nerve gas, explosives, or biological agents. The food industry can also benefit greatly from chemical-biological sensors. Several new sensors have been created in recent years to detect bad fish, *e-coli*, lead and mercury poisoning, heavy metals, bitterness in beer, toxicity in foods, and more. The military requires rapid analysis of a situation for successful operations. The presence of a chemical or biological warfare agent needs to be detected as fast as possible to limit exposure to troops.

Occupational Safety & Health Administration (OSHA) has mandated more environmental monitoring every year. Common environmental monitoring analytes are biological oxygen demand (BOD), atmospheric acidity, pH, detergents, herbicides, and fertilizer concentrations in drainage and river water. Monitoring systems can be installed at sites of potential pollution to limit the spread of pollutants.

The potential for biosensor technology is great, and the potential impact is far reaching. Nature offers a variety of molecules with abilities to recognize chemical and biological substances, from pheromones to environmental odors. These molecules can be utilized for military as well as civilian applications by designing them to specifically bind to chemicals such as those used in explosives, biological agents, or environmental pollutants providing the possibility for a quick, highly specific and inexpensive detection system of these compounds. Research and development in the chemical-biological sensor field combines Chemistry, Biology, Physics, Material Science, Electrical Engineering, and Computer Science. While there are methods which yield detection limits in the parts-per-billion regime in principle, lack of specificity and irregularities due to interferences are problems yet to be solved. Thus, there remain ongoing needs for sensors that solve these deficiencies and also provide inexpensive, compact, and reliable sensors.

SUMMARY

Against the above background, some embodiments described herein are directed to wireless sensors for detection of an analyte. The wireless sensors may include a sensor receiving antenna configured to receive interrogation pulses having an interrogation frequency, a DC converter electrically coupled to the sensor receiving antenna, a relaxation oscillator circuit electrically coupled to the DC converter, and a sensor transmitting antenna electrically coupled to the relaxation oscillator circuit. The relaxation oscillator circuit may include a capacitance element that defines a response-pulse frequency of the wireless sensor. The sensor transmitting antenna may be configured to receive response pulses from the relaxation oscillator circuit and to transmit the response pulses at the response-pulse frequency. The capacitance element of the relaxation oscillator circuit may include an interdigitated capacitor. At least the interdigitated capacitor may be coated with a detection layer of a functional material having a detection-layer dielectric constant that defines an IDC dielectric constant of the interdigitated capacitor. The detection-layer dielectric constant may then change when the functional material is exposed to the analyte, thereby changing the response-pulse frequency of the relaxation oscillator circuit to an analyte-exposure frequency indicative of the exposure of the functional material to the analyte.

Further embodiments described herein are directed to wireless systems for detecting an exposure of a wireless sensor to an analyte. The wireless systems may include an interrogator module that sends interrogation pulses having an interrogation frequency to a wireless sensor and receives response pulses having a response-pulse frequency from the wireless sensor. The wireless sensor may include a sensor receiving antenna configured to receive the interrogation pulses, a DC converter electrically coupled to the sensor receiving antenna, a relaxation oscillator circuit electrically coupled to the DC converter, and a sensor transmitting antenna electrically coupled to the relaxation oscillator circuit. The relaxation oscillator circuit may include a capacitance element that defines the response-pulse frequency. The sensor transmitting antenna may be configured to receive response pulses from the relaxation oscillator circuit and to transmit the response pulses to the interrogator module at the response-pulse frequency. The capacitance element of the relaxation oscillator circuit may include an interdigitated capacitor. At least the interdigitated capacitor may be coated with a detection layer of a functional material having a detection-layer dielectric constant that defines an IDC dielectric constant of the interdigitated capacitor. The detection-layer dielectric constant may change when the functional material is exposed to the analyte, thereby changing the response-pulse frequency of the relaxation oscillator circuit to an analyte-exposure frequency indicative of the exposure of the functional material to the analyte.

Additional features and advantages of the embodiments described herein will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

DETAILED DESCRIPTION

Embodiments of wireless sensors for detection of one or more analytes will now be described with reference to FIGS. 1-3 and 6. Wireless systems incorporating the wireless sensors will be described in detail below with reference to FIGS. 1-6. Data from exemplary wireless systems according to embodiments herein will be described with reference to FIGS. 7-12. The wireless sensors according to exemplary embodiments herein may be used for detection of an analyte, such as chemical and/or biological agents, based on a change of frequency response from the wireless sensor when a functional layer present on the wireless sensor is exposed to the analyte. Thus, the passive wireless sensors may detect chemical or biological agents without the use of probes or wires and without the use of a battery. In general, the wireless sensors may be powered through an interrogator module that sends magnetic or inductive waves to the wireless sensor. The sensor converts the power to direct current and then sends back a portion of the power through radio frequency waves with altered frequency, amplitude, and phase. The characteristics of the received signal contain the information about the analyte of interest.

Figure 1:
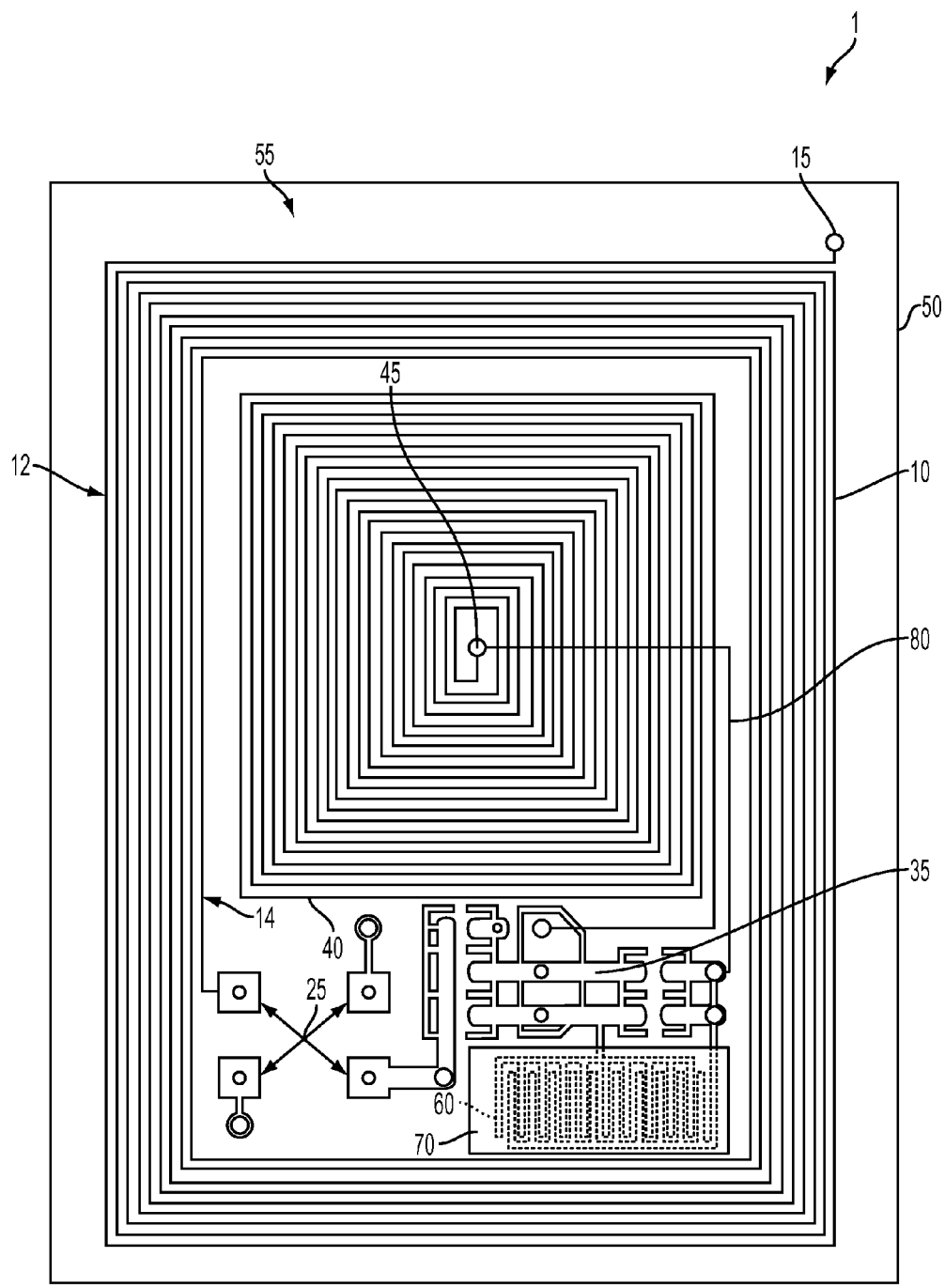
FIG. 1 is a top view of a printed circuit board for a wireless sensor according to some embodiments herein.
Figure 6:
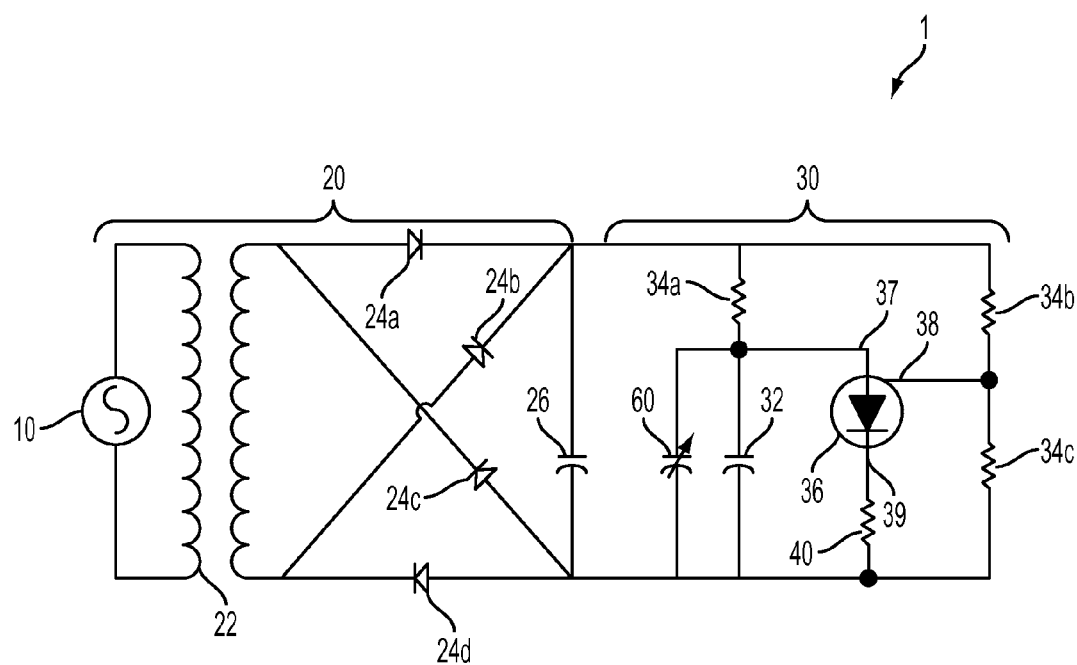
FIG. 6 is a schematic diagram of electrical circuitry in wireless sensors according to embodiments herein.

Referring to FIGS. 1 and 6, a wireless sensor 1 for detection of an analyte may include a sensor receiving antenna 10 configured to receive interrogation pulses having an interrogation frequency. In some embodiments, the interrogation pulses may be in the form of radio-frequency electromagnetic radiation. The interrogation frequency of the radio-frequency electromagnetic radiation may range from about 1 MHz to about 30 MHz, such as from about 1 MHz to about 20 MHz, from about 1 MHz to about 10 MHz, from about 2 MHz to about 8 MHz, or about 5 MHz, for example.

The wireless sensor 1 may also include a DC converter 20 electrically coupled to the sensor receiving antenna 10, a relaxation oscillator circuit 30 electrically coupled to the DC converter 20, and a sensor transmitting antenna 40 electrically coupled to the relaxation oscillator circuit 30. In some embodiments, and as illustrated in FIG. 1, the sensor receiving antenna 10, the DC converter 20, the relaxation oscillator circuit 30, and the sensor transmitting antenna 40 may be provided on a sensor-substrate surface 55 of a sensor substrate 50. The sensor substrate 50 may be a rigid substrate, such as a printed circuit board, or may be any flexible substrate onto which conductive traces can be applied. The sensor substrate 50 may have any practical size, with lengths and widths ranging from tens of centimeters to as small as a few millimeters or even fractions of a millimeter, subject only to the limits of available technologies for laying down antenna patterns.

Each of the sensor receiving antenna 10, the DC converter 20, the relaxation oscillator circuit 30, and the sensor transmitting antenna 40 may be configured in any suitable geometry or arrangement that facilitates size minimization of the wireless sensor 1. In some embodiments, for example, the sensor receiving antenna 10 may define an outer perimeter 12 of the wireless sensor 1 on the sensor-substrate surface 55. In such embodiments, the DC converter 20, the relaxation oscillator circuit 30, and the sensor transmitting antenna 40 may be disposed on the sensor-substrate surface 55 inside an inner perimeter 14 of the sensor receiving antenna 10. It should be understood, however, that the arrangements and geometries exemplified in FIG. 1 are to be considered illustrative only and that numerous other arrangements and geometries are possible as embodiments not specifically shown in FIG. 1.

The sensor receiving antenna 10 may be made of any electrically conductive material such as a metal or a conductive polymer, for example. In some embodiments, the sensor receiving antenna 10 may be made of a metal such as copper or aluminum. The sensor receiving antenna 10 may be configured in any geometry that facilitates conversion of received radio-frequency electromagnetic radiation into electrical signals by induction. Though in FIG. 1 the sensor receiving antenna 10 is shown as a rectangular coil beginning at receiving antenna terminus 15 and having ten windings, it should be understood that many geometries are possible. When the sensor receiving antenna 10 is configured as a coil, the coil may include any practical number of windings, such as from 1 to 100 windings, from 5 to 50 windings, from 10 to 50 windings, or even more than 100 windings, for example. The individual windings may have widths and separations selected to maximize the number of windings that can be fit onto a sensor substrate 50, subject only to the technical constraints of patterning materials onto the type of sensor substrate 50 being used. For example, if a printed circuit board is used as the sensor substrate 50, individual windings may have widths as small as about 0.015 inches (about 0.381 mm) and separations as small as about 0.01 inches (about 0.0254 mm). In general, the sensor receiving antenna 10 may convert radio-frequency electromagnetic radiation from the interrogation pulses into alternating-current electrical signals that are fed into the circuitry of the wireless sensor, which includes the DC converter 20 and the relaxation oscillator circuit 30.

The DC converter 20 of the wireless sensor 1 is electrically coupled to the sensor receiving antenna 10. The DC converter 20 in general converts alternating-current electrical signals from the sensor receiving antenna 10 into pulsing direct-current signals. In some embodiments, the DC converter 20 may be a full-wave bridge rectifier. The pulsing direct-current signals may be converted into continuous direct current by a rectifier capacitor 26, for example, and the continuous direct current may be fed into the relaxation oscillator circuit 30. The alternating-current signals may be stepped down in voltage by a rectifier transformer 22, for example. When a full-wave bridge rectifier is used, the DC converter may also include a plurality of rectifier diodes 24a, 24b, 24c, 24d configured to accomplish the conversion of alternating current into pulsing direct current. In an exemplary embodiment, the DC converter 20 may be seated on the sensor-substrate surface 55 sensor substrate 50 in any suitable location, such as in contact with converter contacts 25, as shown in FIG. 1. Typical voltages received by the DC converter 20 may be in the range of from 1 V to 50 V, for example, but indeed voltages higher than 50 V may be used if other components of the circuitry of the wireless sensor 1 are capable of withstanding such higher voltages.

The relaxation oscillator circuit 30 of the wireless sensor 1 is electrically coupled to the DC converter 20. According to some embodiments, the relaxation oscillator circuit 30 receives the continuous direct current signal from the DC converter 20 and provides response pulses to the sensor transmitting antenna 40 at a response-pulse frequency. The response-pulse frequency of the relaxation oscillator circuit 30 and of the wireless sensor 1 as a whole is dependent at least in part on a capacitance element in the relaxation oscillator circuit 30 that will be described in greater detail below. In the schematic of FIG. 6, for example, the capacitance element includes a variable capacitor and a small capacitor, shown as interdigitated capacitor 60 and small oscillator capacitor 32. In an exemplary embodiment, components of the relaxation oscillator circuit 30 may be seated on the sensor-substrate surface 55 sensor substrate 50 in any suitable location, such as in contact with oscillator circuit traces 35, as shown in FIG. 1.

In exemplary embodiments such as shown schematically in FIG. 6, the relaxation oscillator circuit 30 may include a plurality of oscillator resistors 34a, 34b, 34c, 34d and a unijunction transistor 36 having a UJT anode 37, a UJT cathode 39, and a UJT gate 38. In the relaxation oscillator circuit, the plurality of oscillator resistors 34a, 34b, 34c, the unijunction transistor 36, and the capacitance element (for example, the interdigitated capacitor 60 and the small oscillator capacitor 32) together define the response-pulse frequency of electrical signals sent from the relaxation oscillator circuit 30 into the sensor transmitting antenna 40. The oscillator resistors 34a, 34b, 34c may include an input resistor 34a, and bias resistors 34b, 34c, for example. The input resistor 34a limits the maximum amount of current that can pass through the unijunction transistor 36, and the bias resistors 34b, 34c may reduce the voltage at the UJT gate 38.

The relaxation oscillator circuit 30 shown schematically in FIG. 6 works by charging the capacitance element attached to the UJT anode 37 to a threshold value set by the bias resistors 34b, 34c. The input resistor 34a limits the charge time and also limits valley current to cutoff the unijunction transistor 36 during the discharge segment of operation. When the voltage on the capacitance element rises slightly above the value of the bias resistors 34b, 34c on the UJT gate 38, the unijunction transistor 36 turns on and discharges the capacitive energy through the UJT cathode 39. Because the input resistor 34a limits the amount of current that can flow once the capacitance element discharges, the unijunction transistor 36 shuts off and the cycle starts over again. The unijunction transistor 36 requires a minimum amount of current to flow through it to stay on. This is known as valley current. If the current drops below the valley current threshold, the unijunction transistor 36 turns off.

Thus, during operation of the relaxation oscillator circuit 30, current through the input resistor 34a charges the capacitance element (for example, the interdigitated capacitor 60 and the small oscillator capacitor 32) until the voltage at the UJT anode 37 equals the voltage at the UJT gate 38. Once the voltage at the UJT anode 37 equals the voltage at the UJT gate 38, a response pulse of electric current flows out of the UJT cathode 39 of the unijunction transistor 36 and into the sensor transmitting antenna 40. Such response pulses are generated at a steady response-pulse frequency. In exemplary embodiments, the response pulses may be generated at frequencies such as from 1 Hz to about 250 kHz or from about 10 Hz to about 250 kHz, for example. In a non-limiting embodiment intended for illustrative purposes only, the unijunction transistor 36 may be a 2N6027-type programmable unijunction transistor (General Electric) implemented with a 510 kΩ input resistor 34a, a 27 kΩ first bias resistor 34b, a 16 kΩ second bias resistor 34c, and a small oscillator capacitor 32 (68 pF, for example) in parallel with the interdigitated capacitor 60 to be described in greater detail below. A programmable unijunction transistor is not in fact a traditional unijunction transistor, but rather is a four layer PNPN device that can be configured in a circuit to function as though it were a unijunction transistor. The programmable UJT is called programmable because the bias voltage can be chosen at will, for example, based on the resistance values of the bias resistors 34b, 34c.

The sensor transmitting antenna 40 of the wireless sensor 1 is electrically coupled to the relaxation oscillator circuit 30. As shown in the exemplary embodiment of FIG. 1, the sensor transmitting antenna 40 may be electrically coupled to the relaxation oscillator circuit 30 via a connector line 80 that is connected to an antenna center terminus 45. The connector line 80 may be located underneath the sensor transmitting antenna 40, such as in a separate layer of a multilayer circuit board. The sensor transmitting antenna 40 is configured to receive response pulses from the relaxation oscillator circuit 30 during operation of the wireless sensor 1 and to transmit the response pulses at the response-pulse frequency that is determined by the components of the relaxation oscillator circuit 30, as described above. Thus, the response pulses may be directed from the UJT cathode 39 of the unijunction transistor 36 to the sensor transmitting antenna 40.

The sensor transmitting antenna 40 may be made of any electrically conductive material such as a metal or a conductive polymer, for example. In some embodiments, the sensor transmitting antenna 40 may be made of a metal such as copper or aluminum. The sensor transmitting antenna 40 may be configured in any geometry that facilitates conversion of electric signals from the relaxation oscillator circuit 30 to radio-frequency electromagnetic radiation that is emanated from the sensor transmitting antenna 40, typically to be received by a receiving device not connected to the wireless sensor 1. Though in FIG. 1 the sensor transmitting antenna 40 is shown as a square coil with twenty windings, it should be understood that many geometries are possible. When the sensor transmitting antenna 40 is configured as a coil, the coil may include any practical number of windings, such as from 1 to 100 windings, from 5 to 50 windings, from 10 to 50 windings, or even more than 100 windings, for example. The individual windings may have widths and separations selected to maximize the number of windings that can be fit onto the sensor substrate 50 or within the inner perimeter 14 of the sensor receiving antenna 10, subject only to the technical constraints of patterning materials onto the type of sensor substrate 50 being used. For example, if a printed circuit board is used as the sensor substrate 50, individual windings may have widths as small as about 0.015 inches (about 0.381 mm) and separations as small as about 0.01 inches (about 0.0254 mm).

As described above, the relaxation oscillator circuit 30 includes a capacitance element having at least one capacitor, in which the at least one capacitor includes a variable capacitor such as an interdigitated capacitor 60. In some embodiments, the capacitance element includes the interdigitated capacitor 60 in parallel with at least one additional capacitor, such as a small oscillator capacitor 32. The small oscillator capacitor 32 may be a conventional surface-mount device (SMD) having a small capacitance such as less than 100 pF, for example. Thus, the total capacitance of the capacitance element having capacitors in parallel is the sum of the capacitance values of each of the individual capacitors in the capacitance element. It is believed the small oscillator capacitor 32 may be beneficial as a component that prevents the total capacitance of the capacitance element from dropping to zero in the event that the capacitance of the variable capacitor (e.g., the interdigitated capacitor 60) were to fall to zero for any reason, thereby potentially shorting the relaxation oscillator circuit 30.

Figure 2:
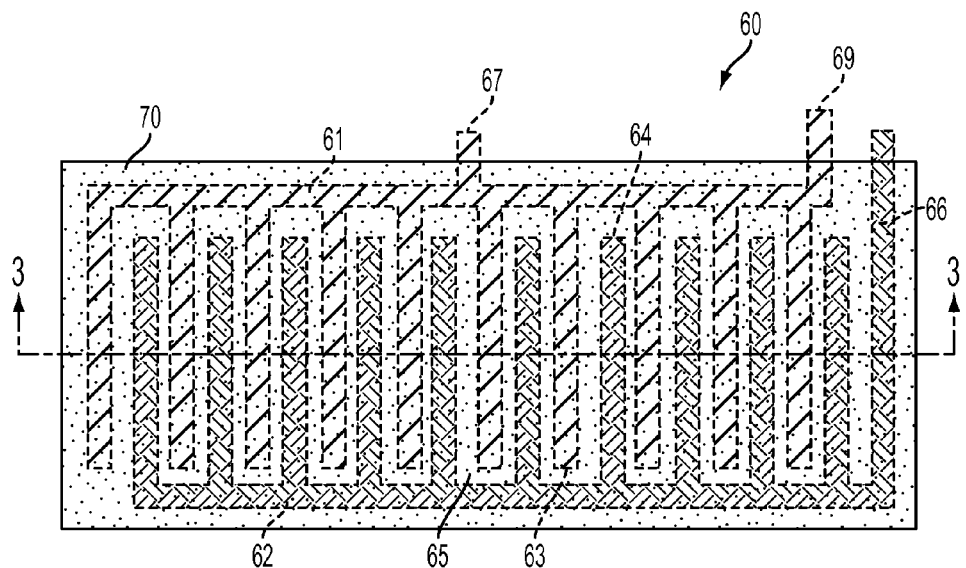
FIG. 2 is a detail view of an interdigitated capacitor that is a component of a capacitance element of wireless sensors according to some embodiments.
Figure 3:
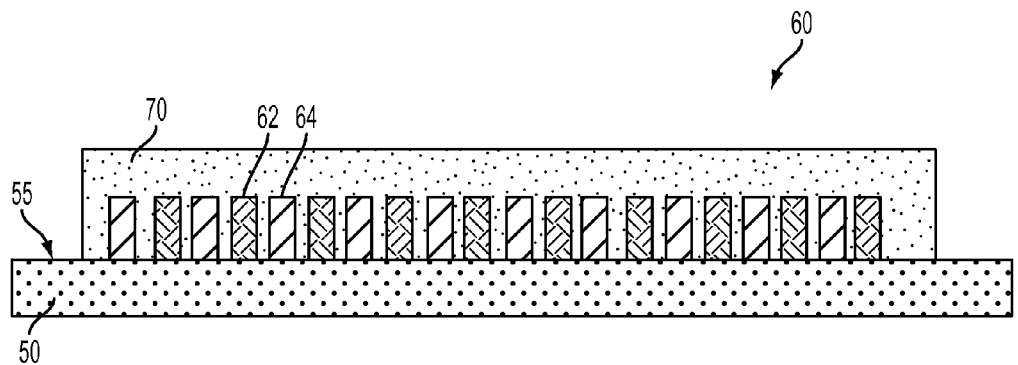
FIG. 3 is a cross-section of the interdigitated capacitor of FIG. 2.

The interdigitated capacitor 60 is shown in greater detail in FIGS. 2 and 3. As shown in FIG. 2, for example, the interdigitated capacitor 60 may include a first capacitor plate 61 and a second capacitor plate 62 substantially parallel to the first capacitor plate 61. The first capacitor plate 61 includes a plurality of parallel first-plate fingers 63, and the second capacitor plate 62 includes a plurality of parallel second-plate fingers 64. With the exception of the first-plate finger on an end of the first capacitor plate 61, each of the first-plate fingers 63 extends between two adjacent second-plate fingers 64, resulting in the "interdigitated" structure resembling fingers of two hands interwoven with each other. Thus, the first-plate fingers 63 are substantially parallel with the second-plate fingers 64. A capacitor-finger gap 65 may be defined between the first-plate fingers 63 and the second-plate fingers 64. The widths of the first-plate fingers 63, the second-plate fingers 64, and capacitor-finger gap 65 each in part determine the capacitance of the interdigitated capacitor 60, along with the detection layer 70 that will be described in greater detail below. In the embodiment of FIG. 2, the interdigitated capacitor 60 may be electrically coupled with the relaxation oscillator circuit 30 through oscillator connections 67, 69 and with the sensor transmitting antenna 40 through antenna connection 66, for example.

Referring to FIGS. 1-3 and 6, in the relaxation oscillator circuit 30 of the wireless sensor 1, at least the interdigitated capacitor 60 may be coated with a detection layer 70. The detection layer 70 may be formed of a functional material having a detection-layer dielectric constant. The detection-layer dielectric constant may define an IDC dielectric constant of the interdigitated capacitor 60 and, thereby, may define the capacitance of the interdigitated capacitor. The capacitance of the interdigitated capacitor 60 may be the primary contribution to the overall capacitance of the capacitance element in the relaxation oscillator circuit 30, which equals the sum of the capacitances of the interdigitated capacitor 60 and the small oscillator capacitor 32. When the detection layer 70 is exposed to an analyte of interest, it is believed that the analyte interacts with the functional material of the detection layer 70 to change the detection-layer dielectric constant. The change of the detection-layer dielectric constant and, accordingly, of the capacitance of the capacitance element, may result in a change the response-pulse frequency of the relaxation oscillator circuit 30 to an analyte-exposure frequency. Thus, when transmitted signals having the analyte-exposure frequency are detected from the sensor transmitting antenna 40, the signals may be interpreted as indicating that an exposure of the functional material to the analyte of interest has occurred.

In some embodiments, the exposure may involve or require only brief contact between the detection layer 70 and the analyte. In other embodiments, the exposure may involve or require immersion of the detection layer 70 into a liquid analyte or may involve or require continued contact for several seconds of the detection layer 70 with a liquid or vapor analyte. Depending on the analyte of interest and the functional material used to coat at least the interdigitated capacitor 60, an exposure of the analyte to the detection layer 70 may result in a temporary or a permanent change of the response-pulse frequency to the analyte-exposure frequency. Also depending on the analyte of interest and the functional material used to coat at least the interdigitated capacitor 60, the response-pulse frequency may be greater than or less than the analyte-exposure frequency. Regardless, for any given configuration of the wireless sensor 1, it is believed that the frequency response of the wireless sensor 1 to any particular analyte will be unique and that an expected change in frequency known in advance through construction of calibration curves and the like will provide a characteristic determination of exposures to the analyte.

In some embodiments, the detection layer 70 itself may be a coating applied by a suitable technique including physical vapor deposition, chemical vapor deposition, dipping, spraying, sputtering, or painting. In exemplary embodiments, the detection layer may have a thickness of from about 1 μm to about 1000 μm, such as from about 5 μm to about 100 μm or about 5 μm to about 50 μm, or about 10 μm to about 100 μm, for example. It should be understood that these thicknesses are illustrative only and that the detection layer 70 may have a thickness greater than 1000 μm or less than 1 μm, particularly if the wireless sensor 1 is very small. In some embodiments, the detection layer 70 may completely cover the interdigitated capacitor 60 and fill the capacitor-finger gap 65 (see FIG. 3, for example). In some embodiments, the detection layer 70 may cover only the interdigitated capacitor 60. In other embodiments, the detection layer 70 may cover the entirety of the sensor-substrate surface 55 of the sensor substrate 50, provided the sensor receiving antenna 10 can still receive signals and the sensor transmitting antenna 40 can still transmit signals.

The functional material of the detection layer 70 may be chosen to have a particular affinity to the analyte of interest, depending on the anticipated manner in which the wireless sensor 1 will be implemented. In any regard, a functional material should be chosen such that the wireless sensor 1 exhibits a noticeable and statistically significant change from the response-pulse frequency of a non-exposed sensor to the analyte-exposure frequency of an exposed sensor.

In some illustrative embodiments, the functional material may be any material that is chemically reactive with the analyte or onto which the analyte physically absorbs or is adsorbed. In other illustrative embodiments, the functional material may be a polymer that is permeable to the analyte. In still other illustrative embodiments, the functional material may be chosen such that when the analyte is hydrophilic, the functional material is also hydrophilic, or, conversely, when the analyte is hydrophobic, the functional material is also hydrophobic. For example, a hydrophilic functional material may provide a detection layer that is sensitive to water present inside an oil pipeline but is unaffected by the oil itself. In still other illustrative embodiments, the functional material may be chosen such that the analyte at least partially dissolves the functional material when the functional material is exposed to the analyte. In such embodiments, the change in frequency of the wireless sensor 1 may be attributable to the differences inherent between a coated interdigitated capacitor and an uncoated interdigitated capacitor.

With regard to the functional material, there has been tremendous growth in the field of polymers that respond to analytes of interest. Certain polymers can exhibit reversible or irreversible changes in physical properties and/or chemical structures to an external stimulus such as pH, temperature, ionic strength, light irradiation, mechanical forces, electric and magnetic fields, specific analytes, external additives (ions, bioactive molecules, etc.), or a combination of these. Responsive polymers can exist in the form of solutions, gels, self-assembled nanoparticles, (multilayer) films, and bulk solids. Applications include the exploitation of useful and advanced functions, e.g., drug or gene carriers with triggered release properties, catalysis, detection and imaging, environmentally adaptive coatings, and self-healing materials. Functional polymeric materials show prominent advantages such as tunable detection sensitivity, structural stability, aqueous dispersibility, biocompatibility, processability, and facile integration into detection devices.

For wireless sensors and microsensors intended for vapor detection, for example, interactive functional coating materials must be chosen that collect and concentrate analyte molecules at the sensor's surface. The sensitivity and selectivity of each individual sensor may be controlled by tailoring the chemical and physical properties of the coating material to maximize particular solubility interactions. The selection of coatings for the complete sensor array is logically made through a systematic variation of the solubility properties of the coating materials, so that each sensor is selective for a different balance of solubility interactions. Parameters and methodologies for characterizing analyte solubility properties, sensor coating material solubility properties, and their interactions, are presented. Specific functional groups are recommended as the functional material to maximize particular interactions. In addition, the treatment-of coating material properties may be integrated with consideration of the factors that influence chemical selectivity in sensor arrays. Functional coating physical and chemical properties that may be considered include, but are not limited to, dispersion interactions, polarizability, dipolarity, hydrogen bond basicity, and hydrogen bond acidity.

In view of the above, exemplary materials for use as the functional material of the detection layer 70 may include dielectric materials such as polymers, ceramics, rubbers, and other materials that are chemically compatible with the interdigitated capacitor 60 and can be coated onto the interdigitated capacitor 60. In non-limiting embodiments, the functional material may be chosen from silk (natural protein, such as from the silkworm species Bombyx mori, for example), Nafion® (sulfonated tetrafluoroethylene, DuPont), acrylic polymers, poly(methylmethacrylate), polystyrene, poly(vinyl chloride), poly(2-chloroethyl vinyl ether), polyacrylamide, polyfluoropolyol (FPOL), poly(ethylenimine) (XPEI), poly(ethylene phthalate) (PEPH), poly(epichlorohydrin) (PECH), poly(isobutylene) (XPIB), phenylmethyl-diphenyisiloxane copolymers, polybis(cyanopropyl)siloxane, poly(ethylene maleate), and poly(butyl acrylate). These particular functional materials may be particularly effective in detecting exposures to broad classes of analytes such as hydrocarbons, petroleum products such as hydraulic fluid or gasoline, chlorine, mineral acids, volatile organics (multiple), pesticides, polychlorinated biphenyls (PCBs), herbicides, alkanes, alkenes, alkynes, dienes, alicyclic hydrocarbons, arenes, alcohols, ethers, ketones, aldehydes, carbonyls, carbanions, polynuclear aromatics, organic derivatives, biomolecules, sugars, isoprenes, isoprenoids, fatty acids, and dimethyl methylphosphonate (DMMP), for example. In other embodiments, the functional material may include nucleotide sequences or protein sequences that will exhibit a predictable response to complementary nucleotide sequences or enzymes in a solution or environment, for example. It should be understood that the foregoing lists of functional materials and analytes are provided as illustrative embodiments only and are not meant to be limiting. Rather, any combination of functional material and analyte may be appropriate for the wireless sensor 1, provided the effects of the analyte on the detection layer 70 and the interdigitated capacitor 60 are detectable, reproducible, and statistically significant.

Embodiments of wireless sensors have been described above. Embodiments of wireless systems for detecting an exposure of a wireless sensor to an analyte will now be described with continuing reference to FIGS. 1-3 and 6, and also with reference to FIGS. 4 and 5. In general, the wireless systems may include an interrogator module that sends interrogation pulses having an interrogation frequency to a wireless sensor and receives response pulses having a response-pulse frequency from the wireless sensor. The wireless sensor 1 may be a wireless sensor according to any of the embodiments that have been described in detail above.

Figure 4:
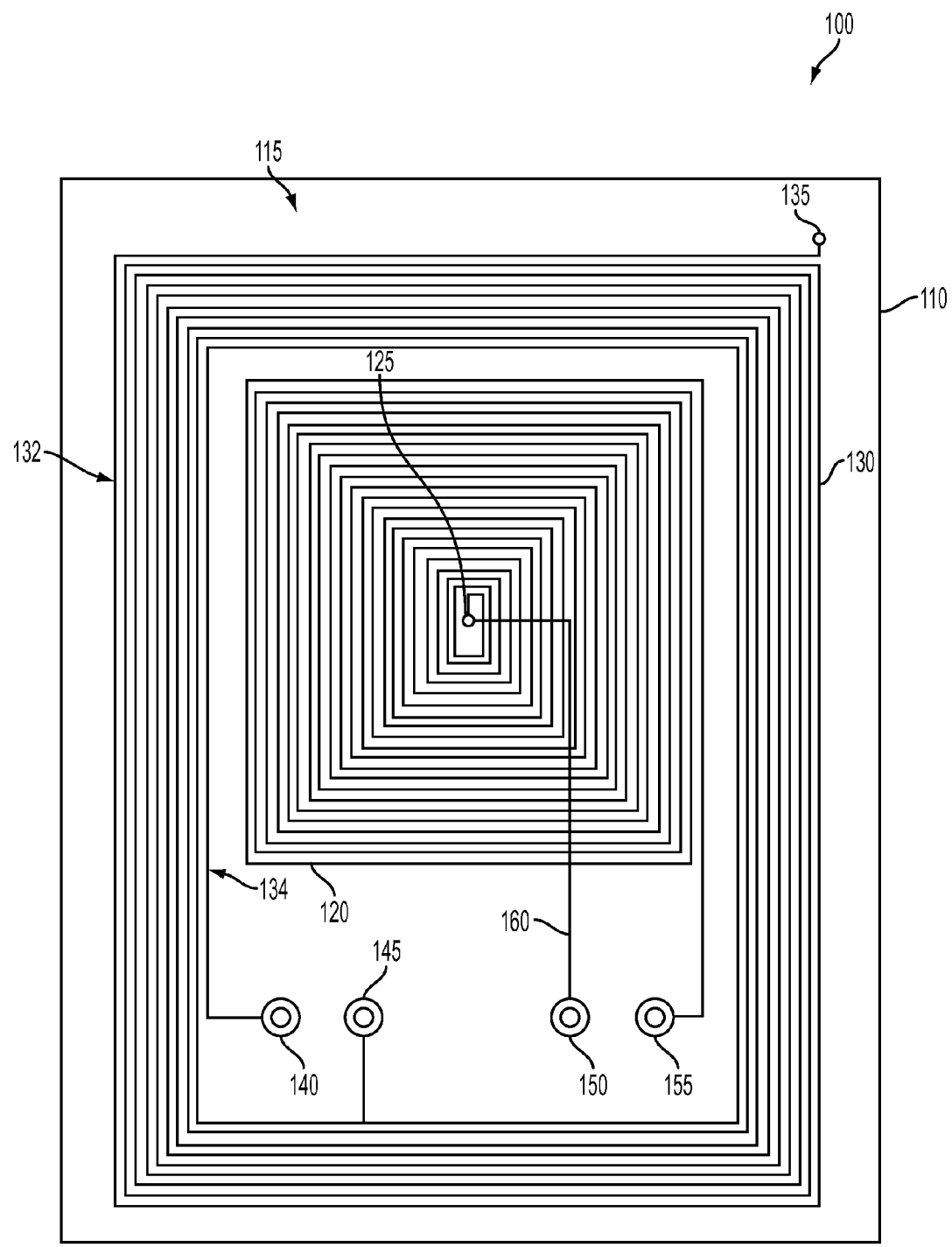
FIG. 4 is a top view of a printed circuit board of a component of an interrogator module according to some embodiments.
Figure 5:
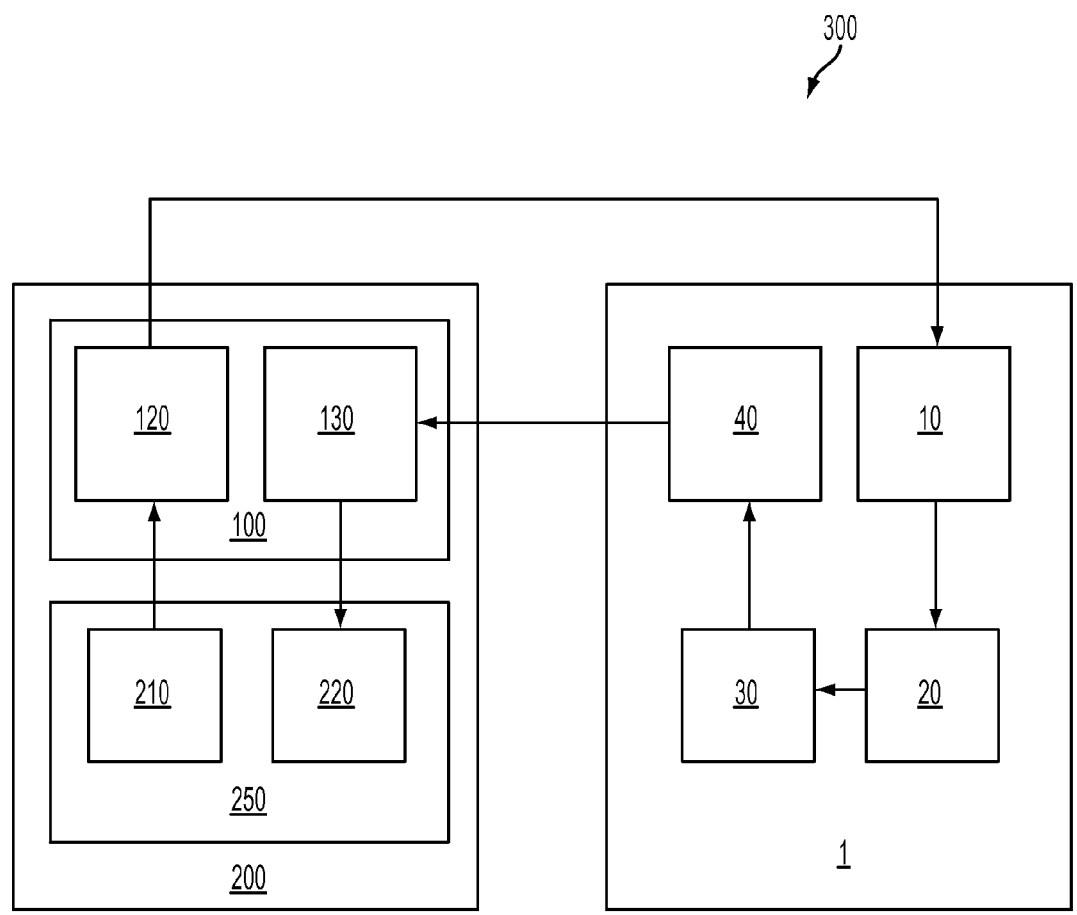
FIG. 5 is a schematic diagram of wireless communication between a wireless sensor and an interrogator module in wireless systems according to embodiments herein.

Referring to FIGS. 4 and 5, the interrogator module 200 may include an interrogator card 100 and an interrogator control device 250. The interrogator card 100 may include an interrogator transmitting antenna 120 and an interrogator receiving antenna 130. The interrogator control device 250 may include at least a radio-frequency generator 210 and a radio-frequency receiver 220. The radio-frequency generator 210 may be electrically coupled to the interrogator transmitting antenna 120 at transmitting antenna contacts 150, 155, connected to opposite ends of the interrogator transmitting antenna 120, for example. The radio-frequency receiver 220 may be electrically coupled to the interrogator receiving antenna 130 at receiving antenna contacts 140, 145, connected to opposite ends of the interrogator receiving antenna 130, for example. The interrogator transmitting antenna 120 may have a transmitting antenna terminus 125 on one end that is connected to a transmitting antenna contact 150 via a contact wire 160 (which may be below the plane of the interrogator transmitting antenna 120 in a multilayer configuration), with an opposite end at a transmitting antenna contact 155, for example. The interrogator receiving antenna 130 may have a receiving antenna terminus 135 on one end, with an opposite end at a transmitting antenna contact 140, for example. The receiving antenna terminus 135 may be connected directly to a receiving antenna contact 145 via a trace that passes underneath the interrogator receiving antenna, of which a portion is shown below receiving antenna contact 145 in FIG. 4. In embodiments not shown, the interrogator module 200 may include additional components such as a visual display that provides frequency information or positive indication of exposure of the wireless sensor 1 to the analyte of interest, as determined by a processor storing relevant data and/or calibration curves.

Similar to the wireless sensors described above, the interrogator transmitting antenna 120 may be configured to send interrogation pulses at an interrogation frequency, and the interrogator receiving antenna 130 may be configured to receive response pulses transmitted from a wireless sensor 1 at a response-pulse frequency that may be an analyte-exposure frequency if the wireless sensor 1 has been exposed to an analyte of interest. The interrogator transmitting antenna 120 may be made of any electrically conductive material such as a metal or a conductive polymer, for example. In some embodiments, the interrogator transmitting antenna 120 may be made of a metal such as copper or aluminum. The interrogator transmitting antenna 120 may be configured in any geometry that facilitates conversion of electric signals from the radio-frequency generator 210 of the interrogator control device 250 to radio-frequency electromagnetic radiation that may be emanated from the interrogator transmitting antenna 120, such that the radio-frequency electromagnetic radiation subsequently may be received by a wireless sensor 1 within proximity of the interrogator module 200. The interrogator receiving antenna 130 may be made of any electrically conductive material such as a metal or a conductive polymer, for example. In some embodiments, the interrogator receiving antenna 130 may be made of a metal such as copper or aluminum. The interrogator receiving antenna 130 may be configured in any geometry that facilitates conversion of radio-frequency electromagnetic radiation received from the wireless sensor 1 back into electrical signals that can be evaluated by the radio-frequency receiver 220 of the interrogator control device 250.

In some embodiments, the interrogator transmitting antenna 120 and the interrogator receiving antenna 130 may be configures as coils provided on an interrogator-substrate surface 115 of an interrogator substrate 110. The number of windings and spacings between windings of the coils may be varied to accommodate the maximum number of windings in the available space, as desired. In some embodiments, the interrogator receiving antenna 130 may define an outer perimeter 132 of the interrogator card 100 on the interrogator-substrate surface 115. In some embodiments, the interrogator transmitting antenna 120 may be disposed on the interrogator-substrate surface 115 inside an inner perimeter 134 of the interrogator receiving antenna 130.

Though not absolutely required in the wireless system 300, in preferred embodiments, the interrogator transmitting antenna 120 of the interrogator card 100 may have an interrogator transmitting-antenna geometry that matches or substantially matches a sensor receiving-antenna geometry of the sensor receiving antenna 10 of the wireless sensor 1. Likewise, the interrogator receiving antenna 130 of the interrogator card 100 may have an interrogator receiving-antenna geometry that substantially matches a sensor transmitting-antenna geometry of the sensor transmitting antenna 40 of the wireless sensor 1. As used here, "geometry" refers to at least one, preferably all, features including number of windings, size and lengths of windings, shape of windings on the respective substrate surfaces, and spaces between windings. As such, in these preferred embodiments, a first antenna that sends information should have a matching or substantially matching geometry with a second antenna that receives signals from the first antenna. It is believed that the matching geometry maximizes the reception of signals and may provide the maximum possible range defining the proximity at which the interrogator module 200 must be placed with respect to the wireless sensor 1 for meaningful signal communication to occur.

Operation of the wireless system 300 according to various embodiments is depicted schematically in FIG. 5. In the interrogator control device 250 of the interrogator module 200, pulses at an interrogation frequency are generated that are sent as electrical pulses into the interrogator transmitting antenna 120 and emanate from the interrogator transmitting antenna 120 as radio-frequency electromagnetic radiation at the interrogation frequency. The as radio-frequency electromagnetic radiation travels through the air to the sensor receiving antenna 10 of the wireless sensor, where it is converted to alternating current. The alternating current is fed from the sensor receiving antenna 10 into the DC converter 20, where it is transformed first into pulsing direct current and then into continuous direct current. The continuous direct current then powers the relaxation oscillator circuit 30 including the capacitance element with the interdigitated capacitor 60 (see FIG. 6) coated with the detection layer 70 (see FIG. 3). Pulsed direct current is fed by the relaxation oscillator circuit 30 into the sensor transmitting antenna 40 at a response-pulse frequency that depends on whether or not the detection layer 70 has been exposed to the analyte of interest. Namely, if the detection layer 70 has not been exposed to the analyte of interest, the sensor transmitting antenna 40 will emanate radio-frequency electromagnetic radiation at a response-pulse frequency. If the detection layer 70 has been exposed to the analyte of interest, the response-pulse frequency will be changed to an analyte-exposure frequency characteristic of the particular analyte of interest. The radio-frequency electromagnetic radiation emanated by the sensor transmitting antenna 40 will then travel through the air to be received by the interrogator receiving antenna 130 of the interrogator card 100 and be converted to electrical pulses that can be discerned or analyzed by the radio-frequency receiver 220 of the interrogator control device 250. If a display (not shown) is present on the interrogator module 200, on receiving the signals from the wireless sensor 1, the interrogator module 200 may be configured to display a positive or negative indication or whether or not the wireless sensor 1 has been exposed to the analyte.

In the wireless system 300, the interrogator module 200 should be able to transmit power to the wireless sensor 1 and also to receive and decode the return signal from the wireless sensor 1 to obtain the intelligence. In various embodiments, different types of waves may be produced using the radio-frequency generator 210. In illustrative embodiments, a sine wave may be used for the transmission. Though sine waves are believed to produce the most power transfer, triangle and/or square waves may also be suitable. The transmitting components of the interrogator module 200 may be either a voltage-controlled oscillator, or a fixed oscillator. If square waves are used for transmissions, the output of a microcontroller on an interrupt loop may also be suitable. In some instances, the impedance of the interrogator transmitting antenna 120 may be very low and may require an amplifier as part of the interrogator module 200 to buffer the output. Though the received signals may contain some feedback from the transmitters in addition to the pulse from the relaxation oscillator output, it is believed that the received pulses may be sufficiently large enough to separate from the carrier feedback, such that a simple comparator may be used as a decoding device in the interrogator module 200. In general, the timing between pulses determines the information from the wireless sensor 1 that is used to ascertain whether an exposure to an analyte of interest has occurred.

Embodiments described above provide a versatile platform for chemical-biological sensors having at least some of the following beneficial features: high sensitivity to the analyte of interest; high specificity to the analyte of interest; stability under normal storage conditions for a good lifetime; good reproducibility over a large number of samples; independence from environmental factors such as temperature, pH, flow, etc; ability to work with minimal chemical interaction; useful range that covers the needed detection levels; accuracy over the useable range of the device; linearity over the useable range of the device; freedom from noise effects; small and portable size; biocompatibility with the working environment; ability to be sterilized; low fabrication and operation cost; and capability of being used by semi-skilled operators. The wireless sensors of embodiments herein do not require wires or batteries, which allows for the chemical-biological sensor to be smaller in size and capable of being placed in solution, under concrete, or in a dangerous environment which can then be measured wirelessly.

EXAMPLES

The embodiments described herein will be further clarified by the following examples.

Wireless sensors and interrogation modules were prepared according to embodiments described above, configured as shown in FIGS. 1 and 4 with circuitry as shown in the schematic of FIG. 6, in which the unijunction transistor 36 was a 2N6027-type programmable unijunction transistor (General Electric) implemented with a 510 kΩ input resistor 34a, a 27 kΩ first bias resistor 34b, a 16 kΩ second bias resistor 34c, and a small oscillator capacitor 32 (68 pF) in parallel with the interdigitated capacitor 60. The wireless sensors were tested for changes in frequency response as a result of exposure of the wireless sensors to various analytes. An 18-loop copper planar coil was used for the sensor transmitting coil and was designed using a 0.015-inch (0.381-mm) wide trace with 0.01-inch (0.254-mm) separation between traces. The outermost edges of the coil measured about 1.7 inches by 2.4 inches (4.3 cm by 6.1 cm). The wireless sensor board and the interrogator board had substantially identical receiving and transmitting antennas.

Figure 7:
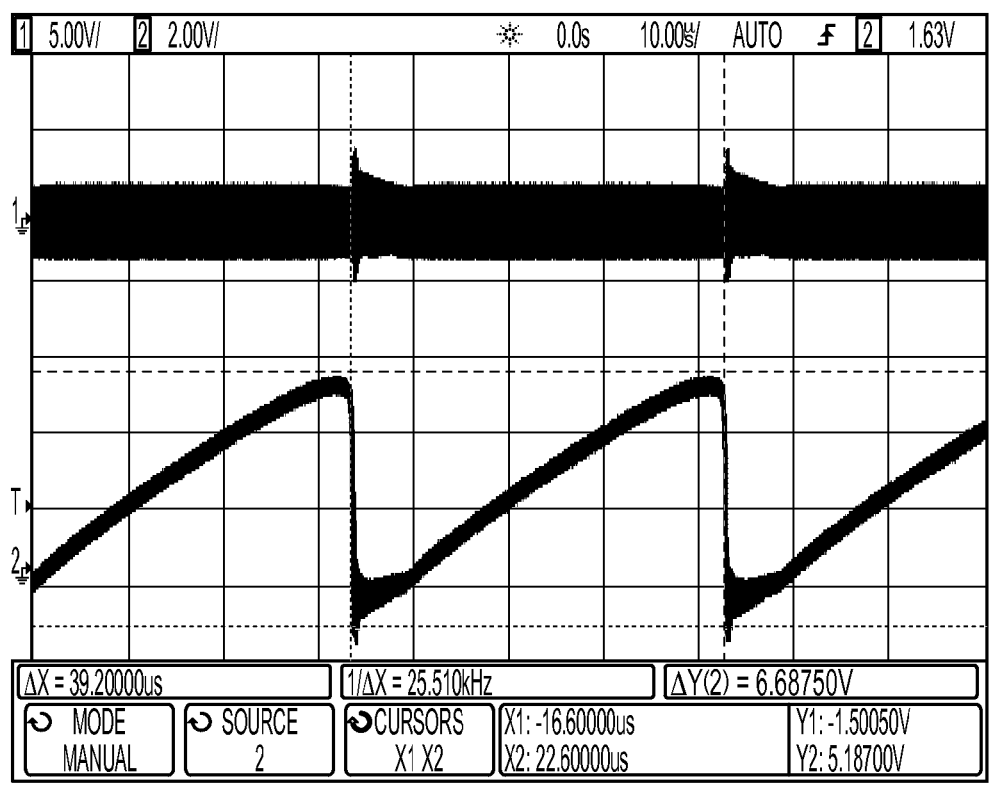
FIG. 7 is a graph of a signal received by an interrogator receiving antenna from a sensor transmitting antenna of a wireless sensor according to embodiments herein.

Analysis of the frequency response of the matched coil sets were performed with a network analyzer. The band of frequencies between 30 MHz and 40 MHz and also around 100 MHz provided a good flat response for the transmitter/receiver pair. The low frequencies around 3 MHz to 10 MHz also provide for a good response. In this sense, a good response means that minimal loss will occur across the pair of antennas at the above-noted frequencies. The spectral response was tested all the way to 3 GHz but did not yield any greater responses. Due to the inner set of antennas' use of a very low frequency in the 30 kHz range, the low frequency behavior was very similar to the outer antennas and, for this reason, the low-frequency spectral response was neglected. The crosstalk behavior from the outer antenna loops to the inner loops were also tested to find an optimal interrogation frequency for sending power with minimal interference on the receiver. A function generator and an oscilloscope were used as the initial interrogator for testing. FIG. 7 illustrates the voltage on the sensor board charge capacitor on the bottom and the return signal to the interrogator on the top.

Figure 8:
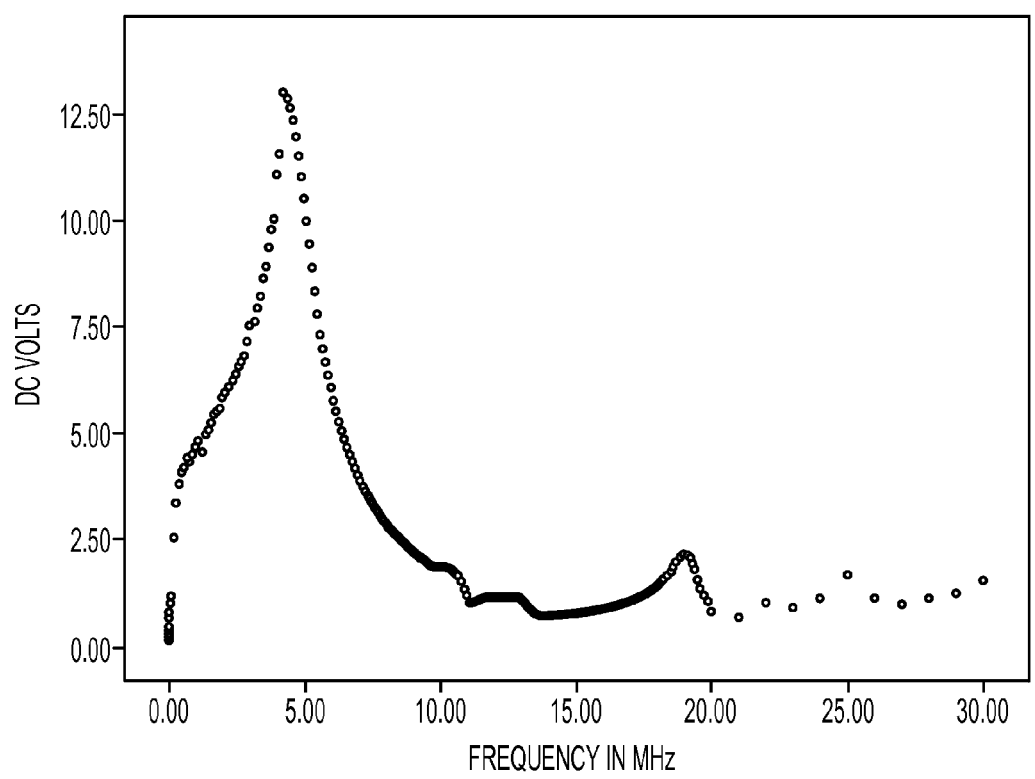
FIG. 8 is a graph of spectral response of inductive power transfer as a function of frequency in an exemplary wireless system according to embodiments herein.

Several of the characteristics of the wireless sensor system were measured and statistically analyzed. The spectral response of the wireless sensor system for inductive power transfer is shown in FIG. 8. The wireless sensor system responded best when the transmitting frequency of the interrogator was in the range of 3 MHz to 6 MHz. Most of the characteristic testing was performed at or around 4.3 MHz.

A voltage test was performed to measure the induced voltage on the sensor board compared with the voltage on the interrogator that was transmitted. The results showed a Pearson correlation of 0.993, which means they were very highly correlated. Twelve samples were collected at each voltage level and compared with each other. Most of the samples had a Pearson correlation of around 0.98, with the lowest correlation being 0.948. The Pearson correlation between the transmitted voltage and the mean frequency of all of the samples was 0.947.

Figure 9:
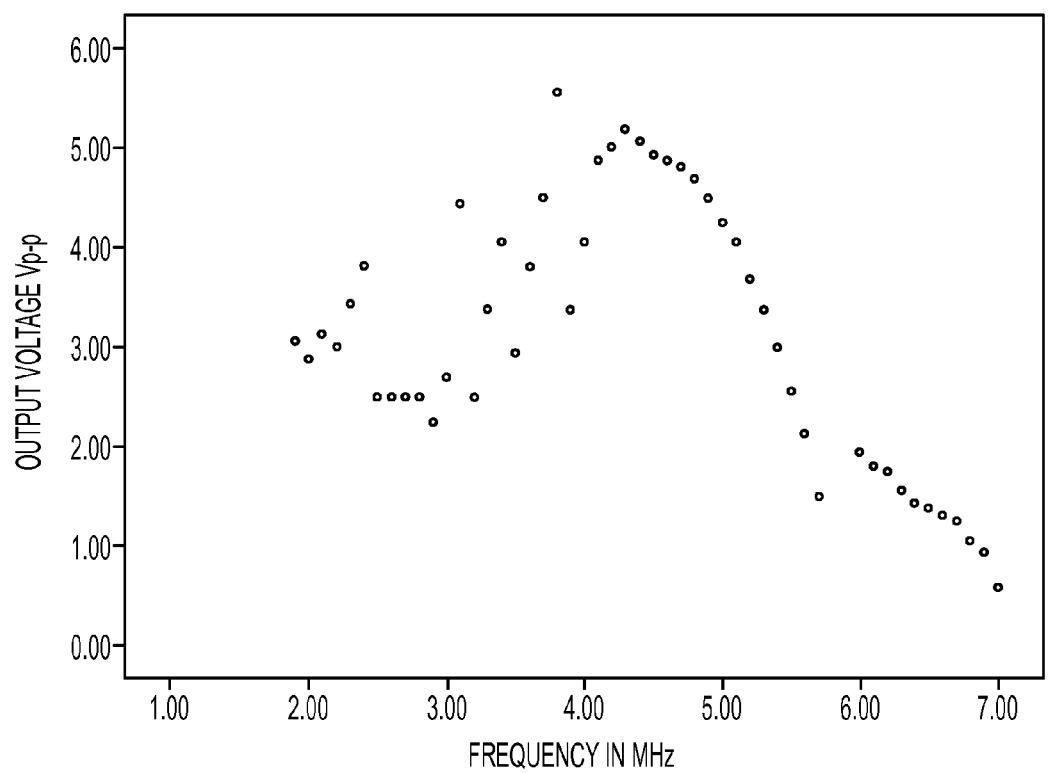
FIG. 9 is a graph of AC spectral response as a function of frequency in an exemplary wireless system according to embodiments herein.

The spectral response of the sensor board's output voltage is shown in FIG. 9, which is similar to FIG. 8 in that the peak response of the platform occurred around 4.5 MHz and in that below 2 MHz and above 7 MHz up to 30 MHz, the sensor board failed to oscillate.

Figure 10:
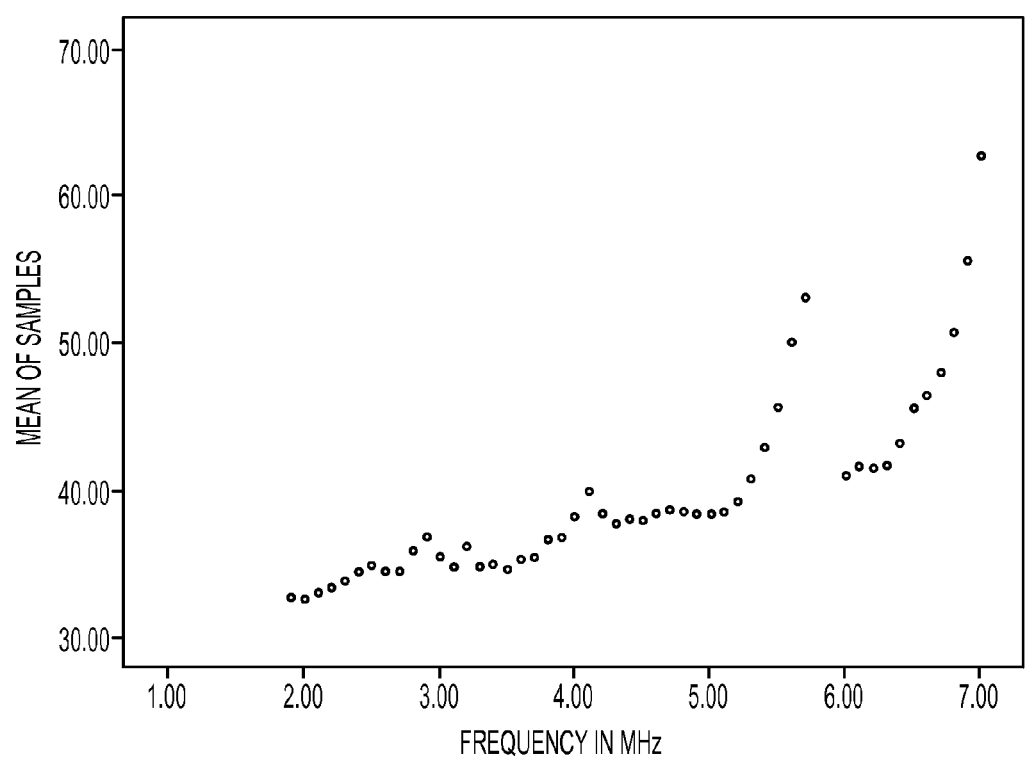
FIG. 10 is a graph of resonant output frequency as a function of input frequency in an exemplary wireless system according to embodiments herein.
Figure 11:
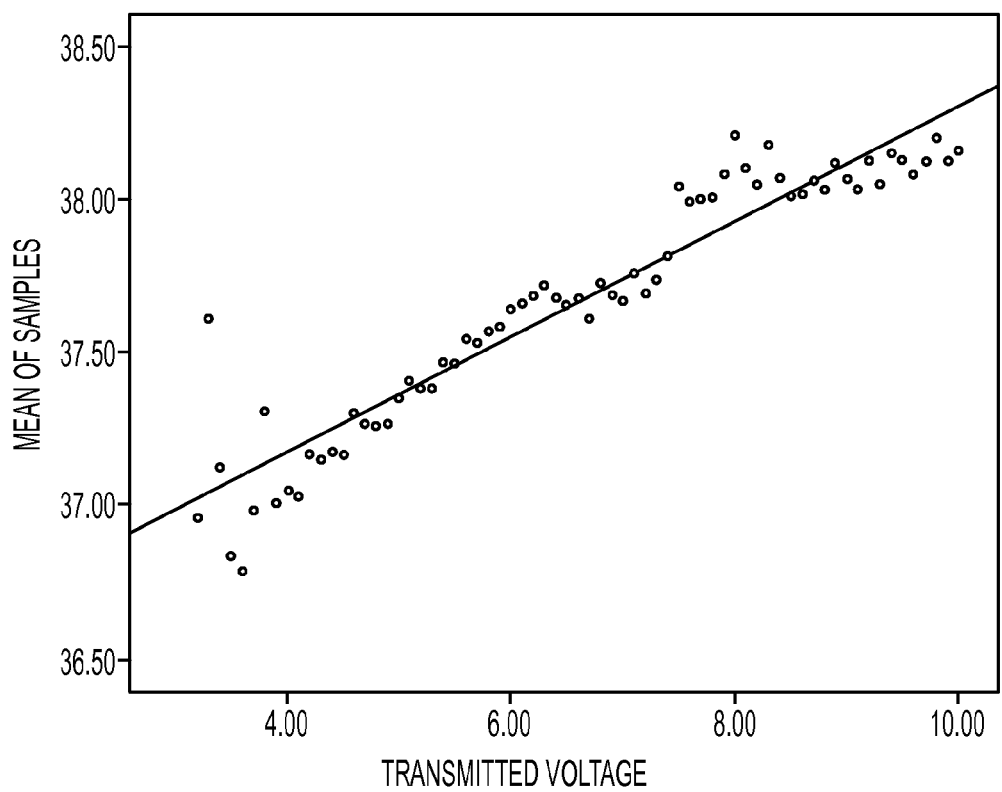
FIG. 11 is a graph of resonant output frequency as a function of input frequency in an exemplary wireless system according to embodiments herein.
Figure 12:
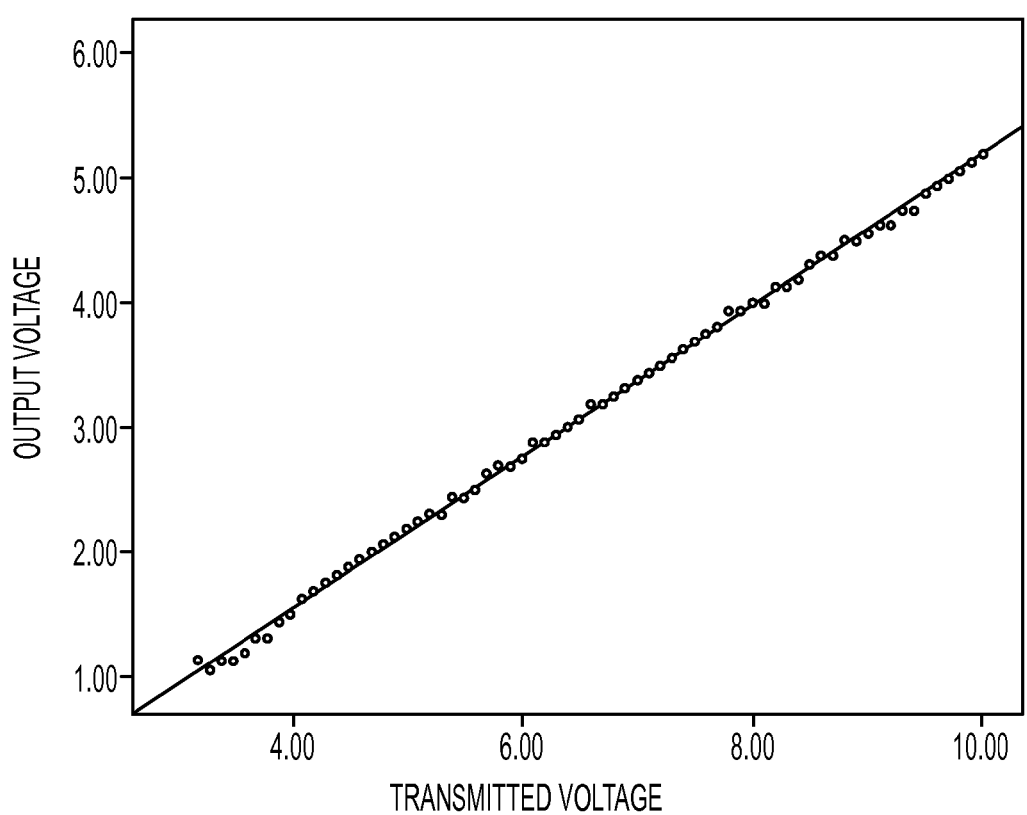
FIG. 12 is a graph of output voltage as a function of input voltage in an exemplary wireless system according to embodiments herein.

The output frequency of the sensor board may be affected by the interrogator transmitting frequency. FIG. 10 shows the mean of the sample frequencies for a given input frequency. The linear regression curve fit of FIG. 10 has a $R^2$ value of 0.846. The output frequency of the sensor board may also be affected by the interrogator transmitting voltage. FIG. 11 shows the mean of the sample frequencies for a given input voltage. The linear regression curve fit of FIG. 11 has a $R^2$ value of 0.897. The relationship between the output AC voltage and the transmitted voltage was extremely linear. FIG. 12 shows the relationship between the output voltage and the transmitted voltage. The linear regression curve fit of FIG. 12 has a $R^2$ value of 0.999.

Repeatability trials were performed to test the impact of placement on the wireless sensor system. A total of 68 trials were performed and the T-test statistical value was 0.541, which means that the differences between the values were insignificant.

Chemical testing was performed on wireless sensors, for which at least the interdigitated capacitor of each wireless sensor was coated with Nafion® (a sulfonated tetrafluoroethylene, DuPont) or silk polymers. There were five boards of each type. One board ("control") was left unaltered, and the other four boards were exposed to an analyte of interest, selected from hydraulic fluid, gasoline, chlorine, and battery acid. All testing was performed wirelessly. The control board for the silk testing showed good repeatability and the control board for the Nafion® testing was not as repeatable.

TABLE 1

Results of chemical testing of wireless sensors

| Analyte | Functional Material | Response-Pulse Frequency | Analyte-Exposure Frequency | T-Test |
|---|---|---|---|---|
| Hydraulic Fluid | Silk | 37.7933 kHz | 36.5510 kHz | 29.234 |
|  | Nafion | 3.1780 Hz | 3.0000 Hz | 10.800 |
| Gasoline | Silk | 38.6867 kHz | 41.6833 kHz | −7.748 |
|  | Nafion | 2.8633 Hz | 2.2403 Hz | 19.347 |
| Chlorine | Silk | 37.0867 kHz | 39.8417 kHz | −120.931 |
|  | Nafion | 2.8553 Hz | 3.7767 Hz | −85.751 |
| Battery Acid | Silk | 36.8400 kHz | 41.8250 kHz | −13.130 |
|  | Nafion | 2.4300 Hz | 2.8550 Hz | −48.817 |
| Control | Silk | 39.3533 kHz | 39.2636 kHz | 2.589 |
|  | Nafion | 3.1773 Hz | 2.5680 Hz | 36.154 |

According to the results for the different chemical tests, some analytes make the resonant frequency of the sensor go up, while others make the resonant frequency go down. Even though the control for the Nafion® testing goes down when re-tested, the Nafion® boards tested with chlorine and battery acid cause the frequency to go up significantly. The effects of chlorine and battery acid are similar on the silk boards. Finally, the results of the fuel cause the frequency to go up on the silk board and down on the Nafion® board. In general, the results from the chemical testing demonstrated that the wireless sensor systems according to embodiments herein do exhibit sensitivity to various analytes by exhibiting a change in frequency characteristics after exposure to the analytes.

Unless otherwise defined, all technical and scientific terms used herein have the same meaning as commonly understood by one of ordinary skill in the art to which the claimed subject matter belongs. The terminology used in the description herein is for describing particular embodiments only and is not intended to be limiting. As used in the specification and appended claims, the singular forms "a," "an," and "the" are intended to include the plural forms as well, unless the context clearly indicates otherwise.

It is noted that terms like "preferably," "commonly," and "typically" are not utilized herein to limit the scope of the appended claims or to imply that certain features are critical, essential, or even important to the structure or function of the claimed subject matter. Rather, these terms are merely intended to highlight alternative or additional features that may or may not be utilized in a particular embodiment.

What is claimed is:

1. A wireless sensor for detection of an analyte, the wireless sensor comprising:
    a sensor receiving antenna configured to receive interrogation pulses having an interrogation frequency;
    a DC converter electrically coupled to the sensor receiving antenna;
    a relaxation oscillator circuit electrically coupled to the DC converter, the relaxation oscillator circuit comprising a capacitance element that defines a response-pulse frequency of the wireless sensor; and
    a sensor transmitting antenna electrically coupled to the relaxation oscillator circuit, the sensor transmitting antenna being configured to receive response pulses from the relaxation oscillator circuit and to transmit the response pulses at the response-pulse frequency;
wherein:
    the capacitance element of the relaxation oscillator circuit comprises an interdigitated capacitor comprising a first capacitor plate including a plurality of parallel first-plate fingers and a second capacitor plate including a plurality of second-plate fingers, a capacitor-finger gap defined between the first-plate fingers and the second-plate fingers, each of the first-plate fingers extending between two of the second-plate fingers to form an interdigitated structure of the interdigitated capacitor;
    the interdigitated capacitor is coated with a detection layer of a functional material having a detection-layer dielectric constant that defines an IDC dielectric constant of the interdigitated capacitor, the detection layer completely covering the interdigitated capacitor and filling the capacitor-finger gap; and
    the detection-layer dielectric constant changes when the functional material is exposed to the analyte, thereby changing the response-pulse frequency of the relaxation oscillator circuit to an analyte-exposure frequency indicative of the exposure of the functional material to the analyte.

2. The wireless sensor of claim 1, wherein the functional coating material is a material that is chemically reactive with the analyte or onto which the analyte physically absorbs or is adsorbed.

3. The wireless sensor of claim 1, wherein the functional material is a polymer that is permeable to the analyte.

4. The wireless sensor of claim 1, wherein the functional coating material is chosen from silk, sulfonated tetrafluoroethylene, acrylic polymers, poly(methylmethacrylate), polystyrene, poly(vinyl chloride), poly(2-chloroethyl vinyl ether), polyacrylamide, polyfluoropolyol (FPOL), poly(ethylenimine) (XPEI), poly(ethylene phthalate) (PEPH), poly (epichlorohydrin) (PECH), poly(isobutylene) (XPIB), phenylmethyl-diphenyisiloxane copolymers, polybis (cyanopropyl)siloxane, poly(ethylene maleate), and poly (butyl acrylate).

5. The wireless sensor of claim 1, wherein the relaxation oscillator circuit further comprises a plurality of resistors and a unijunction transistor, wherein the plurality of resistors, the unijunction transistor, and the capacitance element together define the response-pulse frequency of the relaxation oscillator circuit.

6. The wireless sensor of claim 1, wherein the sensor receiving antenna, the DC converter, the relaxation oscillator circuit, and the sensor transmitting antenna are provided on a sensor-substrate surface of a sensor substrate.

7. The wireless sensor of claim 6, wherein the sensor receiving antenna and the sensor transmitting antenna are coils.

8. The wireless sensor of claim 7, wherein the sensor receiving antenna defines an outer periphery of the wireless sensor on the sensor-substrate surface.

9. The wireless sensor of claim 7, wherein the DC converter, the relaxation oscillator circuit, and the sensor transmitting antenna are disposed on the sensor-substrate surface inside an inner perimeter of the sensor receiving antenna.

10. A wireless system for detecting an exposure of a wireless sensor to an analyte, the wireless system comprising an interrogator module including an interrogator card that sends interrogation pulses having an interrogation frequency to a wireless sensor and receives response pulses having a response-pulse frequency from the wireless sensor, wherein the wireless sensor comprises:
    a sensor receiving antenna configured to receive the interrogation pulses;
    a DC converter electrically coupled to the sensor receiving antenna;
    a relaxation oscillator circuit electrically coupled to the DC converter, the relaxation oscillator circuit comprising a capacitance element that defines the response-pulse frequency; and
    a sensor transmitting antenna electrically coupled to the relaxation oscillator circuit, the sensor transmitting antenna being configured to receive response pulses from the relaxation oscillator circuit and to transmit the response pulses to the interrogator module at the response-pulse frequency;
wherein:
    the capacitance element of the relaxation oscillator circuit comprises an interdigitated capacitor comprising a first capacitor plate including a plurality of parallel first-plate fingers and a second capacitor plate including a plurality of second-plate fingers, a capacitor-finger gap defined between the first-plate fingers and the second-plate fingers, each of the first-plate fingers extending between two of the second-plate fingers to form an interdigitated structure of the interdigitated capacitor;

the interdigitated capacitor is coated with a detection layer of a functional material having a detection-layer dielectric constant that defines an IDC dielectric constant of the interdigitated capacitor, the detection layer completely covering the interdigitated capacitor and filling the capacitor-finger gap; and the detection-layer dielectric constant changes when the functional material is exposed to the analyte, thereby changing the response-pulse frequency of the relaxation oscillator circuit to an analyte-exposure frequency indicative of the exposure of the functional material to the analyte.

11. The wireless system of claim 10, wherein the functional coating material is a material that is chemically reactive with the analyte or onto which the analyte physically absorbs or is adsorbed.

12. The wireless system of claim 10, wherein:
the functional material is hydrophilic and the analyte is hydrophilic; or
the functional material is hydrophobic and the analyte is hydrophobic.

13. The wireless system of claim 10, wherein the analyte at least partially dissolves the functional material when the functional material is exposed to the analyte.

14. The wireless system of claim 10, wherein the functional coating material is chosen from silk, sulfonated tetrafluoroethylene, acrylic polymers, poly(methylmethacrylate), polystyrene, poly(vinyl chloride), poly(2-chloroethyl vinyl ether), polyacrylamide, polyfluoropolyol (FPOL), poly(ethylenimine) (XPEI), poly(ethylene phthalate) (PEPH), poly(epichlorohydrin) (PECH), poly(isobutylene) (XPIB), phenylmethyl-diphenyisiloxane copolymers, polybis(cyanopropyl)siloxane, poly(ethylene maleate), and poly(butyl acrylate).

15. The wireless system of claim 14, wherein the analyte is chosen from hydrocarbons, petroleum products, hydraulic fluid, gasoline, chlorine, mineral acids, volatile organics, pesticides, polychlorinated biphenyls (PCBs), herbicides, alkanes, alkenes, alkynes, dienes, alicyclic hydrocarbons, arenes, alcohols, ethers, ketones, aldehydes, carbonyls, carbanions, polynuclear aromatics, organic derivatives, biomolecules, sugars, isoprenes, isoprenoids, fatty acids, and dimethyl methylphosphonate.

16. The wireless system of claim 1, wherein the interrogator card comprises:
an interrogator transmitting antenna configured to send the interrogation pulses; and
an interrogator receiving antenna configured to receive the response pulses transmitted from the wireless sensor.

17. The wireless system of claim 16, wherein:
the interrogator transmitting antenna and the interrogator receiving antenna are coils provided on an interrogator-substrate surface of an interrogator substrate; and
the sensor receiving antenna and the sensor transmitting antenna are coils provided on a sensor-substrate surface of a sensor substrate.

18. The wireless system of claim 17, wherein:
the interrogator transmitting antenna of the interrogator card has an interrogator transmitting-antenna geometry that substantially matches a sensor receiving-antenna geometry of the sensor receiving antenna of the wireless sensor; and
the interrogator receiving antenna of the interrogator card has a interrogator receiving-antenna geometry that substantially matches a sensor transmitting-antenna geometry of the sensor transmitting antenna of the wireless sensor.

19. The wireless system of claim 16, wherein:
the interrogator transmitting antenna and the interrogator receiving antenna are coils provided on an interrogator-substrate surface of an interrogator substrate;
the interrogator receiving antenna defines an outer periphery of the interrogator card on the interrogator-substrate surface;
the interrogator transmitting antenna is disposed on the substrate surface inside an inner perimeter of the interrogator receiving antenna;
the sensor receiving antenna and the sensor transmitting antenna are coils provided on a sensor-substrate surface of a sensor substrate;
the sensor receiving antenna defines an outer periphery of the wireless sensor on the sensor-substrate surface; and
the DC converter, the relaxation oscillator circuit, and the sensor transmitting antenna are disposed on the sensor-substrate surface inside an inner perimeter of the sensor receiving antenna.

20. The wireless system of claim 16, wherein the interrogator module further comprises:
a radio-frequency generator that generates the interrogation pulses, the radio-frequency generator being electrically coupled to the interrogator transmitting antenna; and
a radio-frequency receiver that determines the response-pulse frequency of incoming response pulses, the radio-frequency receiver being electrically coupled to the interrogator receiving antenna.

* * * * *

UNITED STATES PATENT AND TRADEMARK OFFICE
CERTIFICATE OF CORRECTION

| | | |
|---|---|---|
| PATENT NO. | : 9,177,185 B2 | |
| APPLICATION NO. | : 13/949907 | |
| DATED | : November 3, 2015 | |
| INVENTOR(S) | : Mark Alan Patterson | |

It is certified that error appears in the above-identified patent and that said Letters Patent is hereby corrected as shown below:

In the claims

Col. 18, Claim 18, Line 11,
  "that substantially matches a sensor receiving-antenna" should read
  --that matches a sensor receiving-antenna--; and Col. 18, Claim 18, Lines 15-16,
  "has a interrogator receiving-antenna geometry that substantially matches a sensor transmitting-antenna geom-" should read
  --has an interrogator receiving-antenna geometry that matches a sensor transmitting-antenna geom- --.

Signed and Sealed this
Fifth Day of July, 2016

Michelle K. Lee
*Director of the United States Patent and Trademark Office*